(12) United States Patent
Kato

(10) Patent No.: US 8,894,587 B2
(45) Date of Patent: Nov. 25, 2014

(54) MEDICAL GUIDE WIRE, METHOD OF MAKING THE SAME, AND ASSEMBLY OF BALLOON CATHETER AND GUIDING CATHETER COMBINED WITH THE MEDICAL GUIDE WIRE

(75) Inventor: Tomihisa Kato, Aichi (JP)

(73) Assignee: Asahi Intecc Co., Ltd., Nagoya (JP)

( * ) Notice: Subject to any disclaimer, the term of this patent is extended or adjusted under 35 U.S.C. 154(b) by 1059 days.

(21) Appl. No.: 12/828,973

(22) Filed: Jul. 1, 2010

(65) Prior Publication Data
US 2011/0015570 A1    Jan. 20, 2011

(30) Foreign Application Priority Data
Jul. 2, 2009    (JP) .................. 2009-158152

(51) Int. Cl.
*A61M 25/00*    (2006.01)
*A61L 31/02*    (2006.01)
*A61M 25/09*    (2006.01)

(52) U.S. Cl.
CPC ..... *A61M 25/09* (2013.01); *A61M 2025/09133* (2013.01); *A61L 31/022* (2013.01); *A61M 2025/09083* (2013.01); *A61M 2025/09108* (2013.01)
USPC ........................................................ 600/585

(58) Field of Classification Search
USPC ..................... 600/433, 434, 585; 604/164.13
See application file for complete search history.

(56) References Cited

U.S. PATENT DOCUMENTS

| | | | |
|---|---|---|---|
| 4,538,622 A | 9/1985 | Samson et al. | |
| 5,916,166 A * | 6/1999 | Reiss et al. | 600/434 |
| 5,951,496 A | 9/1999 | Willi | |
| 6,440,129 B1 * | 8/2002 | Simpson | 606/42 |
| 8,211,039 B2 * | 7/2012 | Kato | 600/585 |
| 2004/0167441 A1 | 8/2004 | Reynolds et al. | 600/585 |
| 2005/0022572 A1 | 2/2005 | Kato et al. | |
| 2005/0027214 A1 | 2/2005 | Murayama et al. | 600/585 |
| 2008/0171217 A1 | 7/2008 | Mishima | 428/586 |
| 2009/0182246 A1 * | 7/2009 | Kinoshita et al. | 600/585 |

FOREIGN PATENT DOCUMENTS

| | | |
|---|---|---|
| EP | 1 685 869 A1 | 8/2006 |
| JP | 4-25024 B | 4/1992 |
| JP | 10-513081 | 12/1998 |
| JP | 2001-514544 | 9/2001 |
| JP | 2003-158332 | 5/2003 |

(Continued)

OTHER PUBLICATIONS

Japanese Office Action dated Aug. 18, 2011.

*Primary Examiner* — Max Hindenburg
*Assistant Examiner* — Jonathan M Foreman
(74) *Attorney, Agent, or Firm* — Morgan, Lewis & Bockius LLP

(57) ABSTRACT

In a medical guide wire 1, a flexible core wire 2 is made of austenitic stainless steel wire treated with a solid solution procedure, and drawn with a whole cross sectional reduction ratio as 80%-97.6%. The core wire 2 and a helical spring body 3 are welded by a welding member 4. The welding member 4 is made of eutectic alloy having a melting temperature ranging from 180° C.-495° C. Upon welding the helical spring body 3 to the core wire 2 which is made of the stainless steel metal, the procedure prevents the medical guide wire 1 from sacrificing its mechanical strength by significantly reducing the thermal influence on the core wire 2 and the helical spring body 3.

2 Claims, 16 Drawing Sheets

(56) References Cited

FOREIGN PATENT DOCUMENTS

| JP | 2004-047918 | 2/2004 |
| JP | 2005-014040 | 1/2005 |
| JP | 2006-255396 | 9/2006 |
| JP | 2006-297152 | 11/2006 |
| JP | 2008-188670 | 8/2008 |
| JP | 2009-059941 | 3/2009 |
| WO | WO 96/23441 | 8/1996 |
| WO | 98/39048 | 9/1998 |

* cited by examiner side elevational view side elevational view 2 3    2 1

2 4    2 1 side elevational view cross section along X-X

Fig. 13 side elevational view cross section along F-F cross section along E-E cross section along G-G cross section along H-H

MEDICAL GUIDE WIRE, METHOD OF MAKING THE SAME, AND ASSEMBLY OF BALLOON CATHETER AND GUIDING CATHETER COMBINED WITH THE MEDICAL GUIDE WIRE

BACKGROUND OF THE INVENTION

1. Field of the Invention

The present invention relates to medical guide wire in which a characteristic of mechanical strength is improved at a welded portion between a thin core wire and a helical spring body welded together by means of welding member.

2. Description of Related Art

As a general usage, a distal end of a medical guide wire, i.e., a welded portion between a core wire and a helical spring body requires a specified mechanical strength to insure a safety measure. For this purpose, various types of medical guide wires have been introduced.

In Japanese patent application publication No. 4-25024, a helical spring body has a radiopaque portion and a radiotransparent portion, both of which are placed around a core wire, and screwed at a brazed section between the radiopaque portion and the radiotransparent portion.

This method makes it possible to weld not only helical spring bodies of different types of material but helical spring bodies of stainless steel metal. The stainless steel metal is used to visually recongnize in fluoroscopy. The brazing procedure is used to simply weld the helical spring bodies.

In Japanese patent application publication No. 10-513081, to a distal end portion of a core wire, a helical spring body is secured which has a radiopaque coil portion and a radiotransparent coil portion. The coil portions are welded by means of a laser spot welding, brazing or soldering procedure. So are the coil portions welded to the core wire.

The method makes it possible to weld the core wire to the helical spring body even when either the core wire or the helical spring body is made of the stainless steel metal. By welding both the distal ends of the helical spring body to the respect ends of the core wire, it becomes possible to prevent the helical spring body from being acutely bent at the welded end portions while permitting a helical spring body to move freely at a portion between the welded end sections. The brazing procedure, however, is used to simply weld the helical spring body to the core wire as identified in the above case.

In Japanese Laid-open patent application publication No. 2006-297152, a helical spring body is disclosed which comprises a plurality of thickened wires and secured to a core wire by means of a brazing or soldering procedure. This enables an operator to equally bend the helical spring body at the welded portions. As mentioned in the previous cases, the brazing procedure is also used to simply weld the helical spring body to the core wire.

In the prior art medical guide wires, the brazing procedure functions simply as a welding means upon welding the helical spring body to the core wire (stainless steel wire). No eutectic alloy has been used as a welding member when implementing a brazing or soldering procedure on a core wire. No core wire has been made by drawing a stainless steel wire while considering a thermal influence on the mechanical strength of the core wire.

Therefore, the present invention has been made with the above drawbacks in mind, it is a main object of the invention to provide a medical guide wire which enables an operator to use in safety by improving a tensile strength of the core wire and a welding strength by making use of advantageous effect of the tensile strength due to the thermal influence on the core wire without using the welding member simply as a securement means when the austenitic stainless steel is used to the core wire and is drawn as a wrought-out procedure.

SUMMARY OF THE INVENTION

According to the present invention, there is provided a medical guide wire having a core wire formed of a flexible elongate core member, a helical spring body inserted to the core wire to be placed around the core wire, and a head plug provided at distal ends of the core wire and the helical spring body.

The core wire is made of austenitic stainless steel wire treated with a solid solution procedure, and drawn with a whole cross sectional reduction ratio as 80%-97.6%. The core wire and the helical spring body are partly welded with the use of a welding member. The welding member is represented by a eutectic alloy having a melting temperature ranging from 180° C. to 495° C.

With the above structrue newly conceived in the present invention, it is possible to improve a tensile strength at a welding portion of the core wire by using melting heat of the welding member, thus enabling the core wire to secure a good mechanical strength and welding strength, so that an operator can use the guide wire in safety.

According to other aspect of the present invention, a welding configuration into which the welding member is incorporated comprising the head plug being formed at the distal end of the core wire. The head plug has a film layer coated on an outer surface of the core wire by a predetermined length from the distal end of the core wire, and welded to the distal ends of both the core wire and the helical spring body by means of the welding member.

The structure is such that it is possible to improve a wetting property at the welding portion between the head plug, the core wire and the helical spring body so as to enhance a tensile strength of the core wire while ameliorating a welding strength at the welding section.

According to other aspect of the present invention, the welding member which forms the head plug and the welding member which forms the film layer are identical to or same type of a eutectic alloy.

With the above structure thus attained, it is possible to improve the wetting property at the welding section and insure the same advantages as obtain above.

According to other aspect of the present invention, the eutectic alloy of the welding member forms either a gold metal or a silver metal as a component element. The eutectic alloy of the welding member is 80% gold by weight and 20% tin by weight with a melding temperature as 280° C. Otherwise, the welding member is 3.5% silver by weight and 96.5% tin by weight with a melding temperature as 221° C.

The structure is such that it is possible to improve the tensile strength of the core wire and welding strength at the welding section between the head plug, the core wire and the helical spring body.

According to other aspect of the present invention, the helical spring body is made of a gold metal or made of a platinum-based metal at a welding portion between the head plug and the helical spring body.

The core wire and the helical spring body are welded by the welding member which is made of the eutectic alloy of a gold metal, so as to form the head plug at the distal ends of both the core wire and the helical spring body.

This structure makes it possible to improve the tensile strength of the core wire by using the melting heat of the welding member while ameliorating the welding strength toward the helical spring body with a good corrosive-resistance and visibility each insured.

According to other aspect of the present invention, a medical guide wire has a core wire formed of a flexible elongate member, a helical spring body inserted around the core wire, and a head plug provided at distal ends of both core wire and the helical spring body.

At the drawing step, the core wire is drawn with a whole cross sectional reduction ratio as 80%-97.6%. The core wire is made of austenitic stainless steel wire treated with a solid solution procedure. At the welding step, the core wire and the helical spring body are partly welded by a welding member. At the grinding step, a distal end portion of the core wire is ground, and thereafter a distal end portion of the core wire is polished at the polishing step. At the securing step, the helical spring body is secured to the core wire with the helical spring body placed around the core wire. At the welding step, the core wire and the helical spring body are partly welded by means of a welding member which is made of a eutectic alloy having a melting temperature ranging from 180° C. to 495° C.

The structure is such that it is possible to improve a tensile strength at a welding portion of the core wire by using melting heat of the welding member, thus enabling the core wire to a good mechanical strength and welding strength, so that an operator can use the medical guide wire in safety.

According to other aspect of the present invention, a medical guide wire has a core wire formed of a flexible elongate core member, a helical spring body inserted around the core wire, and a head plug provided at distal ends of the core wire and the helical spring body.

At the drawing step, the core wire is drawn with a whole cross sectional reduction ratio as 80%-97.6%. The core wire is made of austenitic stainless steel wire treated with a solid solution procedure. At the welding step, the core wire and the helical spring body are partly welded by a welding member. At the grinding step, a distal end portion of the core wire is ground. At the securing step, the helical spring body is secured to the core wire with the helical spring body placed around the core wire. At the coating step, a film layer is coated on an outer surface of the core wire by a predetermined length from a distal end portion of the core wire by means of a welding member which is made of a eutectic alloy having a melting temperature ranging from 180° C. to 495° C. At the forming step, the head plug is formed on a distal end of the core wire by means of the welding member. The head plug is welded to the core wire through the film layer, and distal ends of both the head plug and the helical spring body are welded together.

The procedures are such that it is possible to improve a wetting property at the welding portion between the head plug, the core wire and the helical spring body so as to enhance a tensile strength of the core wire while ameliorating a welding strength at the welding section.

According to other aspect of the present invention, at the coating step, a film layer is coated on an outer surface of the core wire by a predetermined length from a distal end portion of the core wire by means of a welding member. At the forming step, the head plug is formed on a distal end of the core wire by welding distal ends of both the head plug and the helical spring body with the use of a welding member. The welding member which forms the head plug and the welding member which forms the film layer are identical to or same type of a eutectic alloy.

With the above procedures thus introduced, it is possible to significantly improve a wetting property at the welding portion between the head plug, the core wire and the helical spring body so as to greatly enhance the tensile strength of the core wire while ameliorating the welding strength at the welding section.

According to other aspect of the present invention, there is provided an assembly of a balloon catheter and a guiding catheter combined with the medical guide wire. An outer diameter of the medical guide wire measures 0.228 mm-0.254 mm which is inserted into the balloon catheter, and the medical guide wire inserted into the balloon catheter is further inserted into the guiding catheter, an inner diameter of which is 2.00 or less.

Due to the fact that the present invention improves the welding strength of the head plug at the welding section, it is possible for the assembly to comply with the request from the market that the head plug should be axially reduced and the helical spring body should be diametrically thinned.

BRIEF DESCRIPTION OF THE DRAWINGS

A preferred form of the present invention is illustrated in the accompanying drawings in which.

DETAILED DESCRIPTION OF PREFERRED EMBODIMENTS

Figure 1:
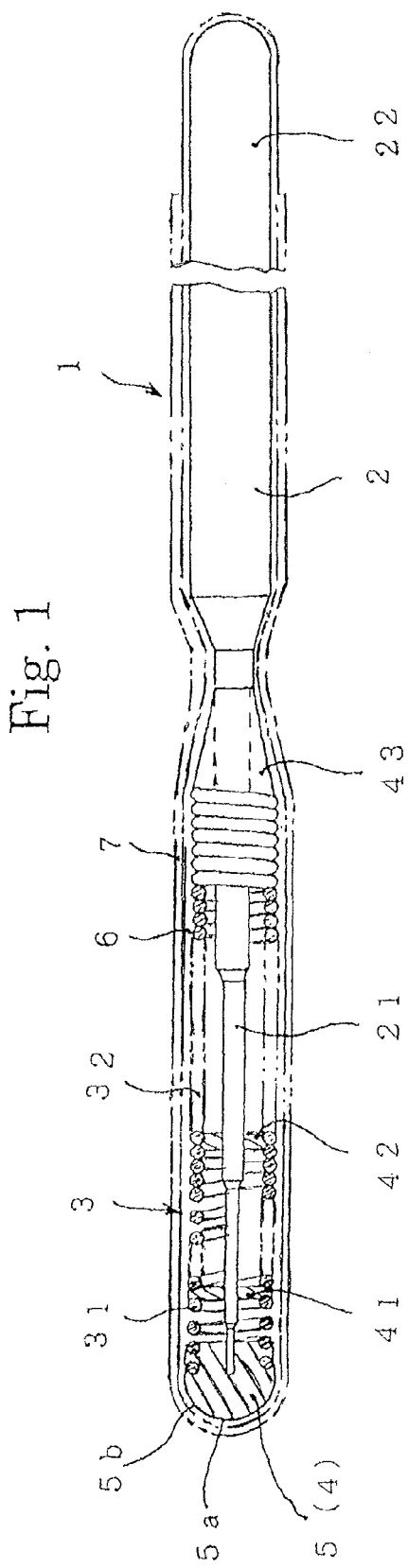
FIG. 1 is an enlarged plan view of a medical guide wire but partly sectioned according to a first embodiment of the invention.

In the following description of the depicted embodiments, the same reference numerals are used for features of the same type.

Referring to FIGS. 1 through 11 which show a medical guide wire 1 (referred to as "guide wire 1" hereinafter) according to a first embodiment of the invention. The guide wire 1 has a core wire 2 formed by a flexible elongate member. The core wire 2 has a distal end portion 21, around which a helical spring body 3 is coaxially placed as shown in FIGS. 1-4.

The helical spring body 3 (simply referred to as "spring body 3" hereinafter) has a distal end portion made of a radiopaque coil 31 (silver, platinum, wolfram, etc.).

Figure 19:
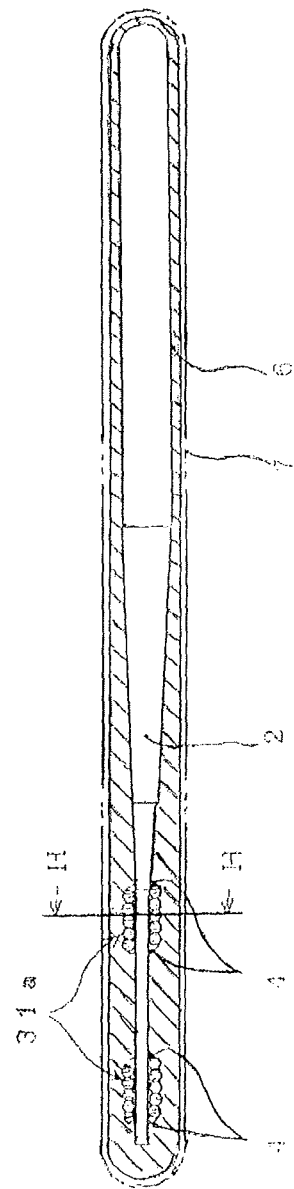
FIG. 19 is a longitudinal cross sectional view of a medical guide wire but partly sectioned according to a fifth embodiment of the invention.

At a front welding section 41, a middle welding section 42 and a rear welding section 43 (refer to FIG. 11) each designated by the distal end portion 21 of the core wire 2, the core wire 2 and the spring body 3 are partly secured by means of a welding member 4 (also refer to FIG. 19).

At a distal extremity of the core wire 2, a head plug 5 is provided which is made of the welding member 4 to connectedly secure the spring body 3 to the core wire 2. The head plug 5 has a semi-spherical portion 5a integrally formed with a short clindrical portion 5b.

The core wire 2 measures around 0.060 mm-0.200 mm in diameter and extends by about 300 mm from the distal extremity of the core wire 2. The rest of the core wire 2 corresponds to a proximal portion 22 made of thicker coil line elements extending approximately 1200 mm-2700 mm.

The distal end portion 21 has a diameter-reduced section, a diameter of which decreases progressively as approaching forward. The diameter-reduced section may be square, rectangular or circular in cross section.

On each of outer surfaces of the core wire 2 and the helical body 3, coated is a film layer 6 which is made of polyurethane, fluorocarbon polymer or other synthetics. The film layer 6 has an outer surface coated with a hydrophilic polymer 7 as a lubricant (e.g., polyvinylpyrrolidone) which exhibits the lubricity when moistened.

The core wire 2 is made of austenitic stainless steel treated as a solid solution, and drawn with a whole cross sectional reduction ratio as 80%-97.6%.

By way of illustration, with the use of several dices, the austenitic stainless steel wire (solid solution wire measuring 1.0 mm-1.5 mm in diameter) is drawn so that its diameter decreases to approx. 0.228 mm-0.340 mm.

During the drawing process, the austenitic stainless steel wire is work hardened and heat treated so that its tensile rupture stress increases from 70 kgf/mm$^2$ to 290 kgf/mm$^2$.

In this instance, when the wire is drawn so that its diameter decreases from 1.5 mm to 0.340 mm, the whole cross sectional reduction ratio comes to 94.8%. When drawn from 1.5 mm to 0.228 mm, the whole cross sectional reduction ratio comes to 97.6%.

The whole cross sectional reduction ratio means a reduction rate R expressed by $R=(S1-S2)/S1$.

Where S1 is a cross sectional area regarding the original diameter of the solid solution wire before the wire is drawn;
S2 is a resultant cross sectional area regarding the finished diameter of the solid solution wire after the wire is drawn.

The tensile rupture stress is represented by $Rp=P1/Sp$.
Where P1 is a magnitude of a tensile force applied when the wire surrenders to disconnection.
Sp is a cross sectional area of the wire when the wire surrenders to disconnection.

Figure 2:
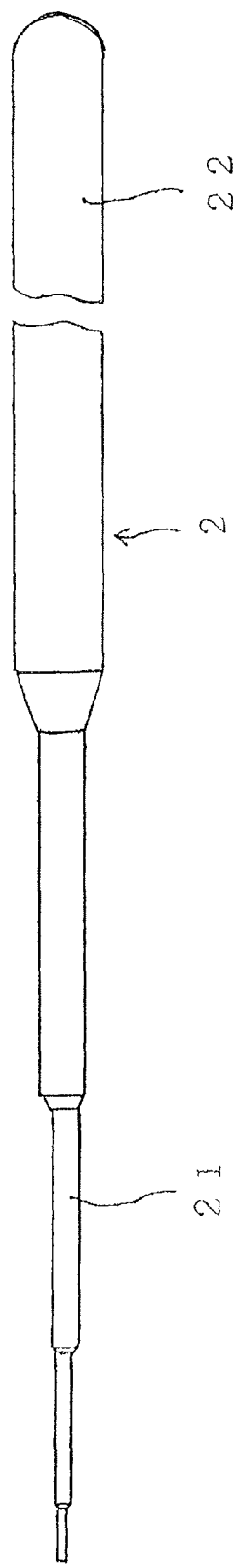
FIG. 2 is an enlarged plan view of a core wire of the medical guide wire.
Figure 3:
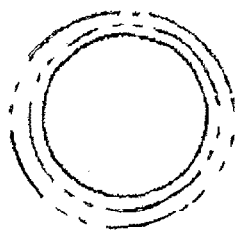
FIG. 3 is a right side elevational view of the medical guide wire.
Figure 4:
FIG. 4 is a right side elevational view of the core wire.
Figure 7:
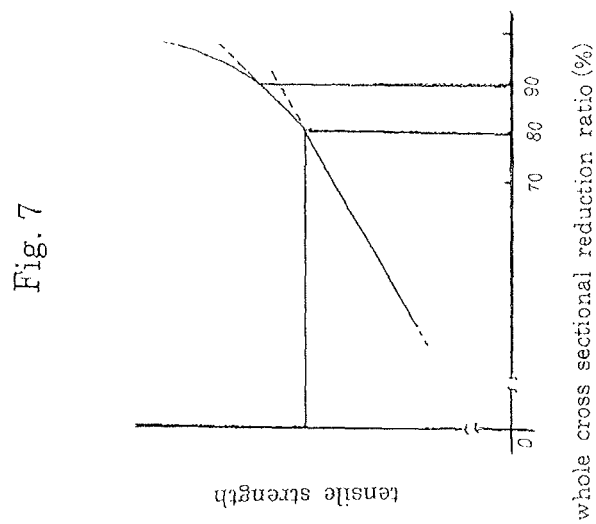
FIG. 7 is a graphical representation of a tensile strength characteristic showing a relationship between a whole cross sectional reduction ratio and a tensile rupture stress.

The whole cross sectional reduction ratio is determined to be 80% or more because the tensile rupture stress abruptly increases when the ratio goes beyond 80% as an inflection point depicted in FIG. 7 (refer to page 63, FIG. 2.82 of "SPRING" (3rd Edition) Published by Maruzen Kabushiki Kaisha in Japan).

It was found in the present invention that the tensile rupture stress more abruptly increases when the ratio goes beyond 90% as the inflection point.

This is because the wire is plastically wrought out strongly during the drawing process, so that the wire develops a fibroid structure when the ratio goes beyond 80%. It seems that the fibroid structure develops exceedingly when the ratio goes beyond 90%.

The whole cross sectional reduction ratio is determined to be 97.6% or less because the wire comes to develop minute voids within its structure to make the structure brittle when the ratio exceeds 97.6% as an upper limit. As described hereinafter in detail, the whole cross sectional reduction ratio is preferably 80%-97.6%, and more preferably 90%-97.6%.

That the austenitic stainless steel wire is drawn as the solid solution, is to attain the austenitic structure superior in workability.

Since it is hard to minutely granulate the crystalloid of the austenitic stainless steel wire by utilizing the transmutational point during the heat treatment process, instead of the heat treatment, the cold working process is used in order to minutely granulate the crystalloid of the austenitic stainless steel wire, and the wire is work hardend to improve the tensile strength during the drawing process.

Another reason to use the austenitic stainless steel wire is that the martensitic stainless steel wire tends to be hardened during the quenching process, and the ferro stainless steel wire tends to be hot-short (sigma brittle, brittle at 475° C.).

At the front welding section 41 of the core wire 2, the radiopaque coil 31 (coil line element measuring 0.060 mm-0.090 mm in diameter) and the core wire 2 (measuring 0.060 mm-0.150 mm in diameter) are welded by the brazing or soldering procedure with the use of the welding member.

At the middle welding section 42 of the core wire 2, the radiotransparent coil 32 (coil line element measuring 0.060 mm-0.090 mm in diameter) and the core wire 2 (measuring 0.150 mm-0.200 mm in diameter) are welded by the brazing or soldering procedure with the use of the welding member.

Between the radiotransparent coil 32 and the core wire 2, an annular disc portion is formed which measures 0.228 mm-0.340 mm in diameter and 0.3 mm-1.5 mm in thickness (width).

At the rear welding section 43 of the core wire 2, the radiotransparent coil 32 (coil line measuring 0.060 mm-0.090 mm in diameter) and the core wire 2 (measuring 0.200 mm-0.340 mm in diameter) are welded by the brazing or soldering procedure. The rear welding section forms a frustoconical configuration, a diameter of which decreases progressively as approaching proximally. Instead of the frustoconical configuration, the rear welding section may be formed into a discal shape which measures 0.228 mm-0.340 mm in diameter and 0.3 mm-3.0 mm in thickness (width).

Figure 5:
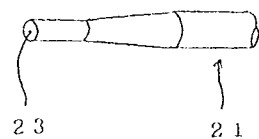
FIGS. 5 and 6 are perspective views each showing a distal end portion of the core wire.
Figure 6:
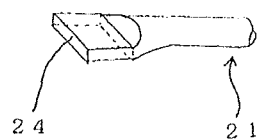

With the use of welding member 4 which forms the head plug 5, the radiopaque coil 31 is welded to a circular end tip 23 (0.060 mm-0.100 mm in diameter) as shown in FIG. 5. Otherwise, the radiopaque coil 31 is welded to a rectangular end portion 24 as shown in FIG. 6. The head plug 5 measures 0.2 mm-1.5 mm in width (length) and 0.228 mm-0.340 mm in diameter.

It is to be noted that the shape of the head plug 5 may be cylindrical, semi-spherical or conical.

Implementing a partly welding procedure means that the head plug 5 is welded to each of the welding sections (41, 42, 43) as the welding member 4.

The core wire 2 has the distal end portion 21 diametrically reduced to measure 0.06 mm-0.200 mm in diameter because the respective distal end portion of the austenitic stainless steel wire (drawn to be 0.228 mm-0.340 mm in diameter) is ground by means of a centerless grinder or the like.

After the austenitic stainless steel wire is drawn, a curve and a torsional strain may be given to the wire with the use of a spinner type rectifier tool or a roller-leveler rectifier tool (not shown), so as to provide a linearity or straightness with the austenitic stainless steel wire. After imparting the linearity or straightness the core wire 2, the wire core 2 may be ground.

Instead of using the spinner type rectifier tool, the distal end portion of the core wire 2 may be energized to be heated by its electrical resistance at low temperature while twisting one end of the core wire 2 with a weight suspended from the other end of the core wire 2.

As the welding member 4, a eutectic alloy is used, a melting temperature of which ranges from 180° C. to 495° C. The eutectic alloy means a special alloyed metal, components of which can be altered to gain a lowest melting temperature.

As a gold-tin based alloy, it contains 80% gold by weight and 20% tin by weight to have the melting temperature (280° C.). As a silver-tin based alloy, it contains 3.5% silver by weight and 96.5% tin by weight to have the melting temperature (221° C.). As a gold-germanium based alloy, it contains 88% gold by weight and 12% germanium by weight to have the melting temperature (356° C.). As gold-tin-indium based alloys, they are represented to have the melting temperature (450° C.-472° C.) as shown in Table 1.

TABLE 1

| Nos. | eutectic alloy (percentage by weight) | melting temp. |
|---|---|---|
| A-1 | 80% gold, 20% tin | 280° C. |
| A-2 | 10% gold, 90% tin | 217° C. |
| A-3 | 88% gold, 12% germanium | 356° C. |
| A-4 | 73.3% gold, 26.7% indium | 451° C. |
| B-1 | 3.5% silver, 96.5% tin | 221° C. |
| B-2 | 40% silver, 30% tin, 30% indium | 450° C. |
| B-3 | 40% silver, 40% tin, 10% indium, 10% copper | 458° C. |
| B-4 | 45% silver, 45% tin, 10% indium | 472° C. |

The reason why the gold is used for the welding member 4 is to improve the visibility in fluoroscopy, the corrosive-resistance and the ductility. The reason why the silver is used is to adjust the melting temperature. The reason why the tin is used is to reduce the melting temperature so as to ameliorate the wetting property with the core wire 2 and the spring body 3. So does the copper and indium are used. The germanium is used because it prevents the intermetallic components from being largely granulated so as to avoid sacrificing the welding strength. It is not preferable to use the lead metal and the stibium metal due to their inappropriate bio-compatibility and poor workability.

The melting temperature is determined to be 180° C.-495° C. because it becomes impossible to improve the tensile strength of the work hardened core wire 2 with the use of the melting temperature (welding member 4) when the temperature is lower than 180° C. When the melting temperature exceeds 495° C., the austenitic stainless steel wire (solid solution wire) begins to be susceptible to the temperature (e.g., 500° C.-850° C.), and resultantly reduces its tensile strength exceedingly as described hereinafter.

By avoiding the susceptive phenomenon of the austenitic stainless steel wire, it becomes possible to maximize the mechanical strength of the core wire 2.

Such is the structure that it becomes possible to increase the tensile strength of the core wire 2 despite the melting heat produced when the core wire 2 and the spring body 3 are welded by means of the welding member 4 (eutectic alloy) although the distal end portion 21 of the core wire 2 is diametrically thin.

Figure 8:
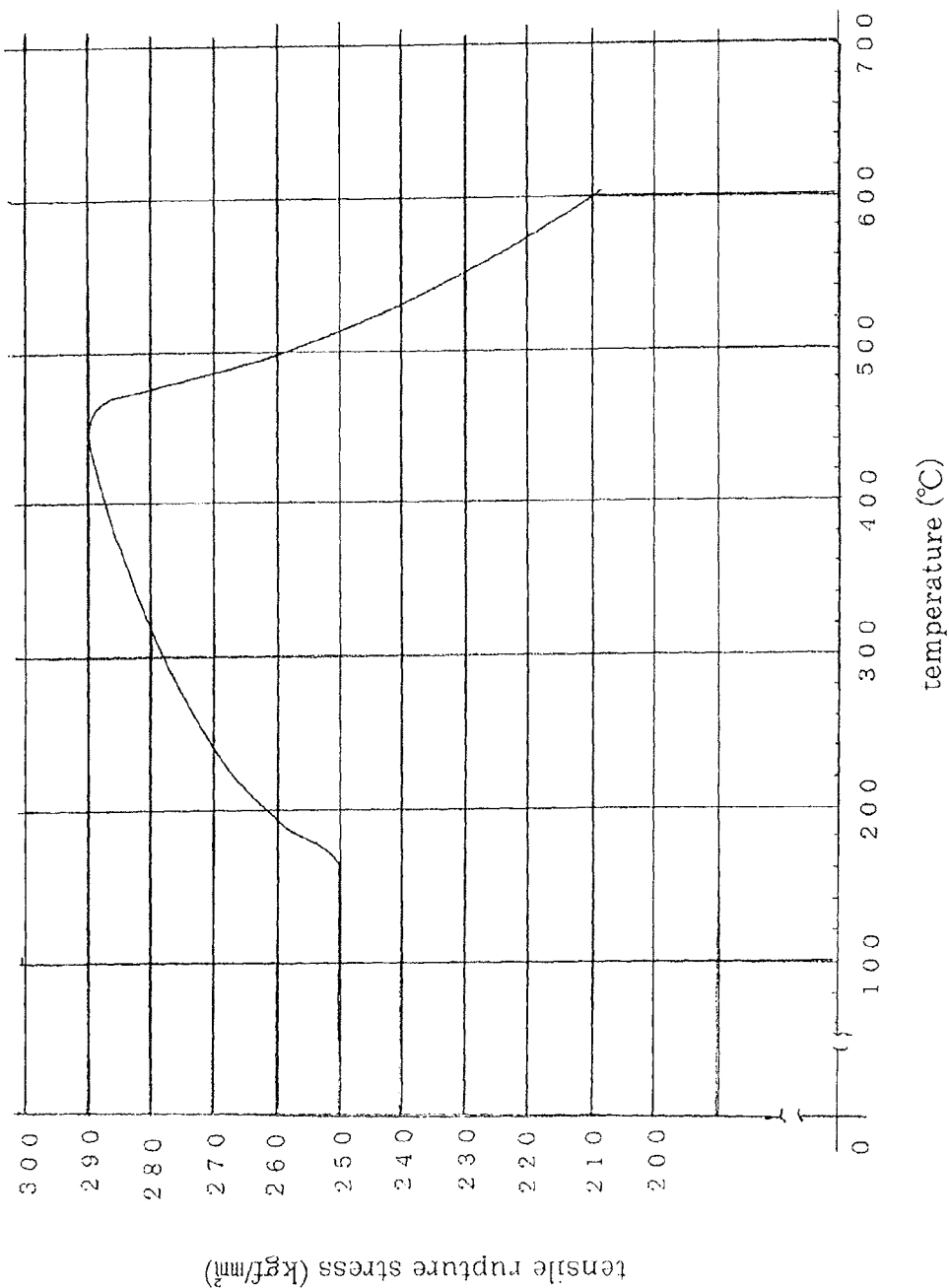
FIG. 8 is a graphical representation of a tensile strength characteristic showing a relationship between a whole cross sectional reduction ratio and temperature.

FIG. 8 shows a characteristic of the tensile strength of the austenitic stainless steel wire (SUS304, 1.5 mm in diameter) treated with the solid solution procedure. The austenitic stainless steel wire is drawn to be 0.340 mm in diameter with the cross sectional reduction ratio as 94.8%. The austenitic stainless steel wire is ground as the core wire 2 to be 0.150 mm in diameter, and heated for 30 minutes in each temperature in FIG. 8.

As observed in FIG. 8, the tensile rupture stress starts to rise at 180° C., and reaches a maximum to continue an improvement of the tensile strength until 495° C. When the temperature exceeds 500° C.-520° C., the temperature abruptly deteriorates the characteristic of the tensile strength in comparison with the core wire treated at the normal temperature (20° C.).

Reasons why the tensile strength deteriorates are as follows:

When the austenitic stainless steel wire is heated to the temperature of 500° C.-850° C., it requires an energy to precipitate the carbon particles and mobilize chromium within the austenitic stainless steel wire (susceptive phenomenon). Especially, for the austenitic stainless steel wire (SUS304) which contains carbon in less than 0.08%, it begins to be susceptible to the thermal influence at 700° C. so as to exceedingly reduce the tensile strength in 4-5 minutes.

Under the condition that the distal end portion 21 of the core wire 2 is susceptible to the thermal influence, the circular end tip 23 (FIG. 5) of the distal end portion 21 approximately measures 0.060 mm-0.150 mm in diameter which is produced by grinding the austenitic stainless steel wire (approx. 0.340 mm in diameter) with the use of the grinder or the like.

As observed by a graphical representation in FIG. 8 the tensile rupture stress 250 kgf/mm$^2$ at the normal temperature rises by circa 6.4% to 266 kgf/mm$^2$ by heating the austenitic stainless steel wire to 180° C.

At the temperature of 450° C., the tensile rupture stress rises by circa 16% to 290 kgf/mm$^2$ (maximum value). By converting the tensile rupture stress to the tensile strength with the use of the cross sectional area, the distal end portion 21 of the core wire increases its tensile strength by 113 gf from 706 gf to 819 gf.

At the temperature of 495° C., the tensile rupture stress rises to 260 kgf/mm$^2$, about 4% increase compared to the tensile rupture stress at the normal temperature.

When the temperature exceeds 500° C.-520° C., the susceptive phenomenon appears to reduce the tensile strength, so that the tensile rupture stress comes to 210 kgf/mm$^2$, meaning that the tensile strength significantly decreases from 819 gf to 593 gf so as to collapse the distal end portion 21 at an exceedingly low tensile strength.

Unless the welding member 4 (eutectic alloy) is used with the tensile strength characteristic taken into consideration, the core wire 2 deteriorates its tensile strength due to the melting heat generated from the eutectic alloy when the core wire 2 and the spring body 3 are welded despite the core wire 2 is work hardened to increase the tensile strength during the drawing process. The reduced tensile strength may separate the head plug 5 from the core wire 2 due to the bending fatigue while navigating the guide wire 1 through the vasculature.

By only drawing the core wire 2 with the whole cross sectional reduction ratio as 94.8%, it is not sufficient to impart the high tensile strength to the core wire 2 with the use of the austenitic stainless steel wire (solid solution) as observed in FIG. 8.

By way of example, a primary procedure is implemented by consecutively drawing the austenitic stainless steel wire (1.5 mm in diameter) through tens of dices (10-20), each of which is capable of drawing with the whole cross sectional reduction ratio as 6%-20%.

During the drawing process, the core wire is drawn with the whole cross sectional reduction ratio as 88.9%. After heat treating the core wire at 400° C.-450° C. (low temperature) for 20-120 minutes, a secondary procedure is implemented by consecutively drawing the core wire (0.340 mm in diameter) through the several dices (5-8) with the whole cross sectional reduction ratio as 53.8%. The latter procedure is repeated depending on the situation until the whole cross sectional reduction ratio comes to 94.8% with the desired tensile strength achieved in the distal end portion 21 of the core wire 2.

During the above processes of drawing the austenitic stainless steel wire until the whole cross sectional reduction ratio reaches 94.8%, the core wire (1.5 mm in diameter) has the tensile rupture stress (70 kgf/mm$^2$) which increases to 215 kgf/mm$^2$ with the whole cross sectional reduction ratio as 88.9% (secondary procedure). While treating the core wire at low temperature (450° C.) for 30 minutes, the core wire 2 reaches the tensile stress to 290 kgf/mm$^2$.

In the graphical representation in FIG. 8, the characteristic of the tensile strength is obtained under the thermal influence when the core wire (0.340 mm in diameter) is ground to be 0.150 mm in its diameter. As the core wire becomes thinner, the shorter the time required to heat treat the core wire at low temperature due to the difference of calorific capacity.

It is preferable that the whole cross sectional reduction ratio (70%-90%) in the primary procedure is greater than the whole cross sectional reduction ratio (45%-80%) in the secondary procedure upon providing the high tensile strength with the core wire 2 and improving the productivity.

The austenitic stainless steel wire of the present invention has chemical composition as follows:

C: less than 0.15% by weight, Si: less than 1.0% by weight, Mn: less than 2.0% by weight, Ni: 6%-16% by weight, Cr: 16%-20% by weight, P: less than 0.040%, S: less than 0.030%, Mo: less than 3.0%, balance: iron and impure substances unavoidably contained.

Without using a high silicic stainless steel (Si: 3.0%-5.0% by weight), it is possible to provide the core wire 2 with the high tensile strength by making it from the austenitic stainless steel wire.

Table 2 shows how the tensile rupture stress changes depending on the whole cross sectional reduction ratio under the constant temperature at 450° C. An increment ratio in Table 2 means a comparison with the tensile rupture stress based on the whole cross sectional reduction ratio (70%). When the whole cross sectional reduction ratio is 90%, the increment ratio comes to 1.32 (264/200).

TABLE 2

| | reduction ratio (%) | | | |
|---|---|---|---|---|
| | 70 | 80 | 90 | 94.8 (invention) |
| tensile rupture stress (max) kgf/mm$^2$ | 200 | 226 | 264 | 290 |
| increment ratio | 1 | 1.13 | 1.32 | 1.45 |

As observed from Table 2, when the whole cross sectional reduction ratio is 80%, the tensile rupture stress increases by 1.13 fold compared to the counterpart when the whole cross sectional reduction ratio is 70%, and develops the inflection point at which the tensile rupture stress increases. With the increases of the whole cross sectional reduction ratio (90%), it further develops another inflection point at which the tensile rupture stress abruptly increases, and exhibits a non-linear characteristic as observed in FIG. 7

Resultantly, it is preferable to determine the whole cross sectional reduction ratio to be 80%-97.6%, more preferably 90%-97.6% in order to weld the core wire 2 by means of the welding member while maintaining the high tensile strength for the welding section.

The eutectic alloy is employed to the welding member 4 upon welding the core wire 2 which is improved in its tensile strength by drawing the austenitic stainless steel wire. The eutectic alloy has a melting point ranging from 180° C. to 495° C., the range of which corresponds to the optical tensile rupture stress of the core wire 2.

This makes it possible to weld the core wire 2 by utilizing the melting heat from the eutectic alloy while maximizing the tensile strength of the core wire 2. The melting temperature of the welding member 4 is determined to be within the range of 180° C.-495° C. because it is possible to strongly weld the core wire 2 within the respective temperature range while utilizing the melting heat of the welding member 4 to increase its tensile strength.

Upon forming the head plug 5 from the welding member 4, the core wire 2 also increases its tensile rupture stress due to the melting heat of the welding member 4. In accompany with the tensile rupture stress being increased, it becomes possible to avoid the possibility of separating the head plug 5 from the core wire 2 even if the operator repetitively bends the core wire 2 while navigating the guide wire 1 through the vasculature.

On the other hand, when the silver brazing metal (melting temperature: 605° C.-800° C.) or the gold brazing metal (melting temperature: 895° C.-1030° C.) is employed to the welding member 4, the core wire becomes brittle due to the susceptive phenomenon or annealed to significantly reduce its tensile rupture stress, thus increasing the possibility of coming the head plug off the core wire due to the reduced tensile strength and bending stress.

This holds true when employing the gold brazing metal (melting temperature: circa 880° C., gold: 74.5%-75.5% by weight, silver: 12.0%-13.0% by weight, Zn, Fe, Pb: less than 0.15% by weight), and the silver brazing metal (melting temperature: circa 780° C., silver: 72.0% by weight, copper: 28.0% by weight).

Since the core wire 2 has the characteristic of the tensile rupture stress as exhibited in FIG. 8, after drawing the austenitic stainless steel wire until it comes to have the final diameter, the austenitic stainless steel wire may be straightened with the use of the spinner type rectifier tool, and thereafter heat treated at low temperature of 380° C.-495° C.

Then, the distal end portion 21 of the core wire 2 is ground to weld it to the spring body 3 with the use of the welding member 4 so as to increase the tensile strength of the core wire 2.

In lieu of using the spinner type rectifier tool, the distal end portion 21 of the core wire 2 may be energized to be heated by its electrical resistance at low temperature (380° C.-495° C.) while twisting one end of the core wire 2 with a weight suspended from the other end of the core wire 2 in an aim to straighten the core wire 2.

In this instance, the reason why the core wire 2 increases its tensile strength is that the melting heat (180° C.-495° C.) of the welding member 4 equalizes the concentrated stresses locally developed on the core wire 2 upon applying the spinner type rectifier tool to the core wire 2 or upon twisting the core wire 2 under the tensile weight applied.

It is preferable to use the melting temperature of the welding member 4 within the range of 220° C.-480° C., more preferably 280° C.-480° C. in which the core wire 2 significantly increases its tensile strength.

The core wire 2 is improved at its characteristic of the tensile strength due to the melting heat from the welding member 4 after pressing the distal end portion 21 to be rectangular in cross section. This procedure makes it possible to increase the welding strength between the rectangular section of the distal end portion 21 and the head plug 5, the latter of which is made of the same alloy as the welding member 4.

The reason why the distal end portion 21 increases its welding strength against the head plug 5 is that the melting heat of the welding member 4 equalizes the concentrated stress developed on the distal end portion 21 due to the straightening and impressing procedures, and additionally enlarges the contact area between the rectangular section and the head plug 5 due to the increased circumferential length of the rectangular section.

Following are procedures of welding the spring body 3 to the distal end portion 21 of the core wire 2, and forming the head plug 5 with the use of the welding member 4 (eutectic alloy).

The austenitic stainless steel wire (SUS304) treated with the solid solution procedure, is drawn so that the stainless steel wire decreases its diameter from 1.5 mm to 0.340 mm. The distal end portion 21 of the core wire 2 is ground so that the distal end portion 21 (rear welding section 43) measures approximately 0.200 m in diameter.

The distal end portion 21 is further thinned by means of the centerless grinder so that the distal end portion 21 progressively decreases its diameter from 0.100 mm to 0.060 mm as approaching forward. An extremity of the distal end portion 21 is plastically pressed to form the circular end tip 23 or the rectangular end tip 24 each shown in FIGS. 5 and 6.

The rectangular end tip 24 may be a flat plate measuring 0.094 mm in width and 0.030 mm in thickess, or may be shaped into a multi-stepped configuration having different widths and thicknesses.

The spring body 3 is formed by coil line elements, each diameter of which measures 0.060 mm-0.090 mm. The spring body 3 has the front radiopaque coil 31 and the rear raidotranspanrent coil 32. The former is made of gold, platinum or gold-plating, and the latter made of stainless steel or the equivalents.

After drawing the distal end portion 21 of the core wire 2, the distal end portion 21 is ground which is thereafter electrolytically polished or treated with the use of a paper file or an abrasive. The spring body 3 is coaxially inserted to the distal end portion 21 to be placed around the distal end portion 21 of the core wire 2.

Figure 9:
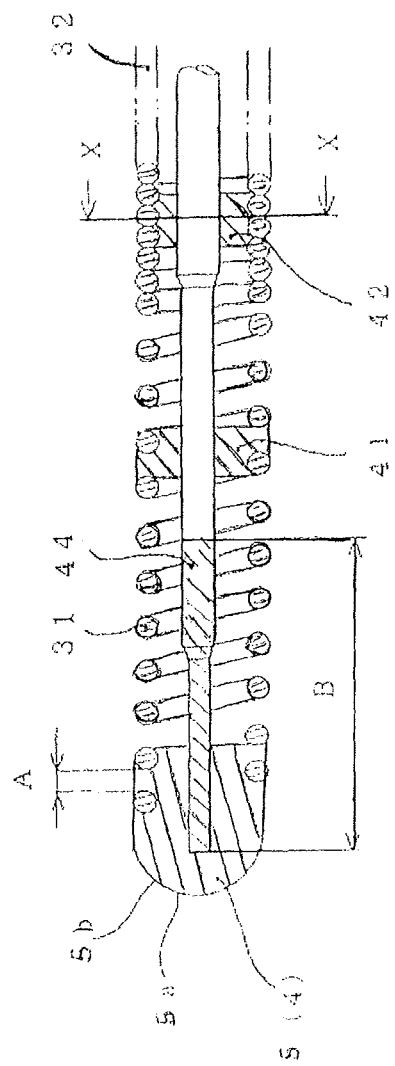
FIG. 9 is a longitudinal cross sectional view of the distal end portion of the medical guide wire.
Figure 10:
FIG. 10 is a left side elevational view of the medical guide wire.
Figure 11:
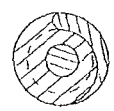
FIG. 11 is a latitudinal cross sectional view taken along the line X-X of FIG. 9.

As shown in FIG. 9, the film layer 44 is coated on an outer surface of the distal end portion 21 of the core wire 2 by the length (B) proximally from the extremity of the distal end portion 21 by melting the eutectic alloy of the welding member 4.

With the use of the welding member 4 which has the identified or the same eutectic alloy as used to the film layer 44, the core wire 2 and the spring body 3 are partly welded. At a welded section in which a distal extremity end of the distal end portion 21 and a distal end of spring body 3 are welded together, the semi-spherical head plug 5 is formed.

The eutectic alloy same as the welding member 4 means that the gold, silver or tin, otherwise identified two of them occupy 50% (by weight) or more of a total components of the eutectic alloy. In Table 1, the eutectic alloys designated by A1 and A2 are of the same type, but those designated by A1 and B1 belong to different types of eutectic alloys.

It is to be noted that the polishing procedure may be implemented after grinding the core wire 2 which was drawn, after grinding the core wire 2 which was straightened or after grinding the core wire 2 which was heat treated at low temperature (380° C.-495° C.).

Upon forming the head plug 5 with the use of the welding member 4 (FIGS. 9, 10), from the distal end of the core wire 2 proximally, the spring body 3 has 3-10 winds which have a clearance (A) as an interlinear gap between the neighboring coil lines of the spring body 3.

The clearance (A) has a width which measures 8%-90% of the coil lines of the spring body 3. On the distal end portion 21 of the core wire 2, the film layer 44 is coated to be 0.002 mm-0.010 mm in thickness, and extends by the length (B: 5 mm-20 mm) with the use of the eutectic alloy of the welding member 4.

Then, the welding member 4 is used which has the identified or the same eutectic alloy as used to the film layer 44. The welding member 4 is in the form of a semi-spherical or bar-like configuration (0.20 mm-0.30 mm in diameter), and melted to flow on the film layer 44 by permeating the welding member 4 through the interlinear gap of the spring body 3, so as to weld the core wire 2 and the spring body 3 at their distal tip ends.

The welding member 4 thus molten is cooled to be solidified to form the head plug 5, a front end of which is polished to form a smooth spherical surface with the use of an abrasive machine (not shown).

With the structure thus far described, the welding procedures make it possible to solidify the welding portion between the core wire 2 and the spring body 3, thereby significantly improving the welding strength therebetween by forming the head plug 5 with the welding member 4.

The reason why the distal end portion 21 of the core wire 2 is ground before melting the eutectic alloy of the welding member 4, is that the core wire 2, especially which is drawn with the whole cross sectional reduction ratio as 90% or more, comes to extremely deteriorate the witting property with the welding member 4. By electrolytically polishing the distal end portion 21, it becomes possible to remove an oxidized compound there from, thus improving the wetting property with the welding member 4 to increase the welding strength of the welding member 4.

By polishing the core wire 2 along its longitudinal direction with use of the paper file, it is possible to levelize the latitudinal injuries incurred on the core wire 2 when the centerless grinder is used. This prevents the fatigue-based collapse, and improves the fatigue-resistant property so that the core wire 2 can withstand against its repetitive bending operation, to which the core wire 2 is subjected upon therapeutically navigating the guide wire 1 in the vasculature.

The reason why the clearance (A) is provided between the coil lines of the spring body 3, is to facilitate the welding member 4 to flow from the spring body 3 to the core wire 2, and move the welding member 4 spirally along the clearance (A) to meet the core wire 2 with an enlarged contact area in a limited distance.

Since the welding member 4 and the film layer 44 on the distal end portion 21 have the identified or the same type of eutectic alloy, by flowing the welding member 4 on the film layer 44 along the distal end portion 21 of the core wire 2, it is possible for the welding member 4 to improve the wetting property and the fluidity of the welding member 4 against the film layer 44, thereby making it possible to increase the welding strength between the core wire 2 and the spring body 3 with the use of the head plug 5.

When the spring body 3 has the front radiopaque coil 31 made of the gold metal or the gold-plating, it becomes possible to improve the wetting property so as to increase the welding strength between the core wire 2, the spring body 3 and the head plug 5 by employing the eutectic alloy (e.g., A1-A4) to the welding member 4 and the film layer 44.

Before applying the guide wire 1 to the medical treatment, the guide wire 1 is usually dipped in the physiological saline solution. For this reason, the silver sulfide appears on the head plug 5 to darken the head plug 5 within one hour or so after dipping the guide wire 1 when the silver-based eutectic alloy is used to the head plug 5.

With the passage of time, the silver sulfide deeply darkens the head plug 5 to decrease the welding strength due to the corrosion.

In order to avoid the above inconvenience, it is preferable to employ the gold-based eutectic alloy to the welding member 4 which makes visible in the fluoroscopy. By using the gold or gold-based material to the spring body 3, it becomes a preferable configuration to improve the wetting property with the head plug 5 because the material of the spring body 3 is the identified type or the same as used to the head plug 5.

Figure 12:
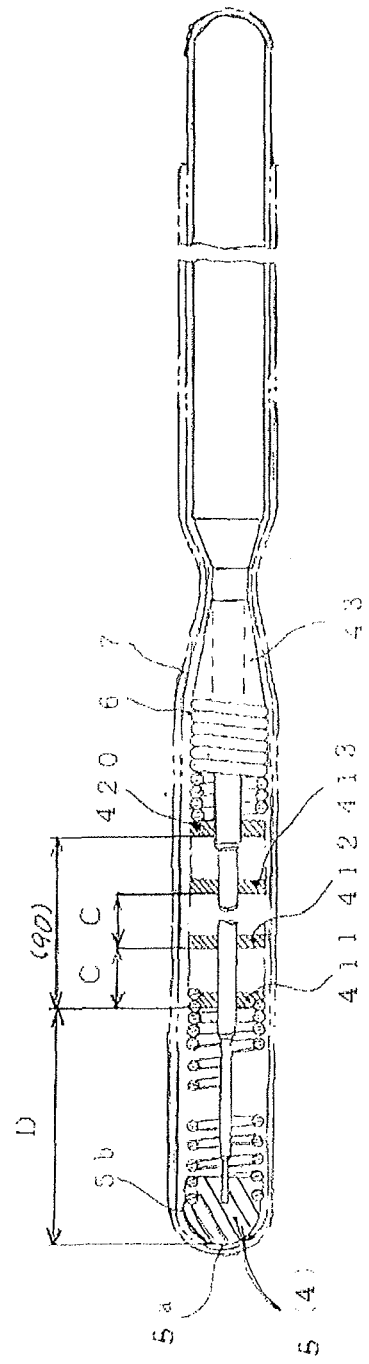
FIG. 12 is an enlarged plan view of the medical guide wire but partly sectioned according to a second embodiment of the invention.
Figure 13:
FIG. 13 is a right side elevational view of the medical guide wire.

FIGS. 12, 13 show a second embodiment of the invention in which ten middle welding sections 411-420 are provided between the core wire 2 and the spring body 3 with the use of the welding member 4.

These middle welding sections 411-420 are arranged longitudinally at regular intervals (C) by a predetermined length (e.g., 90 mm) proximally from a distance (e.g., 50 mm) off the distal extremity of the spring body 3.

By narrowing a mutual distance between the neighboring middle welding sections 411-420, it becomes possible to treat the welding member 4 at low temperature.

In this instance, since not only usable is the melting heat when the core wire 2 and the spring body 3 are welded but also usable is the melting heat when employing the welding member 4, it is possible to increase the tensile strength of the core wire 2 with the use of the melting heat.

With the structure mentioned above, it becomes possible to improve a part of the core wire 2 without using a heating furnace (not shown). With the middle welding sections 411-420 arranged at regular intervals, it becomes possible to dimensionally measure the length of the stenotic lesion in fluoroscopy.

Figure 14:
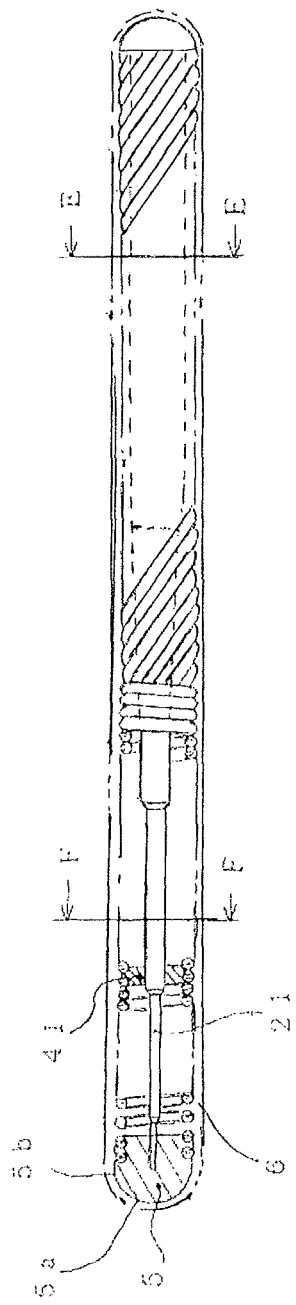
FIG. 14 is an enlarged plan view of a medical guide wire but partly sectioned according to a third embodiment of the invention.
Figure 15:
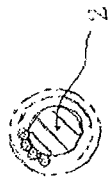
FIG. 15 is a latitudinal cross sectional view taken along the line F-F of FIG. 14.
Figure 16:
FIG. 16 is a latitudinal cross sectional view taken along the line E-E of FIG. 14.

FIGS. 14 through 16 show a third embodiment of the invention in which the spring body 3 has a plurality of coil line elements (length: circa 900 mm-2400 mm) stranded around the proximal portion of the core wire 2. In the third embodiment of the invention, the guide wire 1 has the same structure as the first embodiment of the invention as far as the guide wire 1 extending by 300 mm from the distal extremity of the core wire 2.

Figure 17:
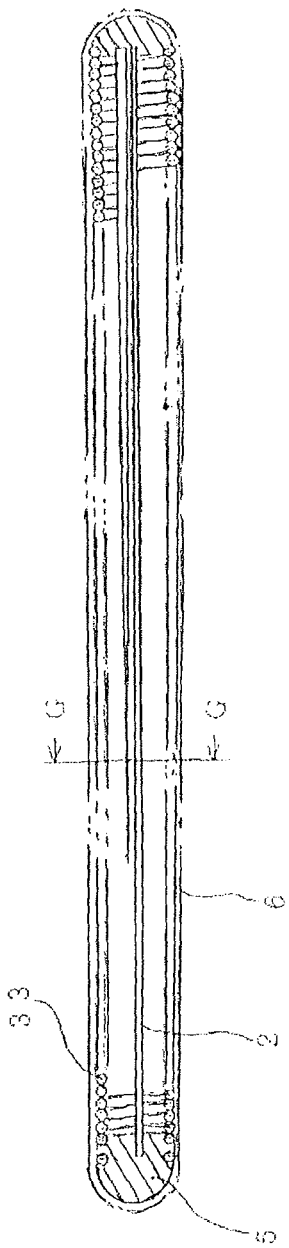
FIG. 17 is an enlarged plan view of a medical guide wire but partly sectioned according to a fourth embodiment of the invention.
Figure 18:
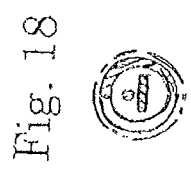
FIG. 18 is a latitudinal cross sectional view taken along the line G-G of FIG. 17.

FIGS. 17, 18 show a fourth embodiment of the invention in which a helical spring body 33 is placed around the core wire 2 along an entire length of the core wire 2. The distal end (proximal end) of the core wire 2 and the distal end (proximal end) of the helical spring body 33 are welded by means of the welding member 4.

Figure 20:
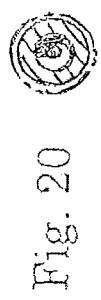
FIG. 20 is a latitudinal cross sectional view taken along the line H-H of FIG. 19.

FIGS. 19, 20 show a fifth embodiment of the invention in which short radiopaque coils 31a are placed around the distal end portion 21 of the core wire 2. Each of the radiopaque coils 31a has front and rear ends each welded to the core wire 2 by means of welding member 4. On outer surfaces of the short radiopaque coils 31a, the film layer 6 is coated. Three or more short radiopaque coils 31a may be provided at regular intervals along the distal end portion 21 of the core wire 2.

According to the third to fifth embodiments of the invention, it is possible to diametrically thin the core wire 2 of the guide wire 1 by using the improved mechanical strength of the core wire 2 and the spring body 3 which are welded by the welding member 4.

By way of illustration, the improved mechanical strength makes it possible to thin the proximal portion 22 of the guide wire 1 from 0.355 mm to 0.254 mm (0.014 inches to 0.010 inches), and further to 0.228 mm (0.009 inches).

Upon implementing the therapeutical treatment against the vascular stenosis, the guide wire 1 is inserted into a balloon catheter (not shown), and the guide wire 1 inserted into the balloon catheter is further inserted into a guiding catheter (not shown) together with the balloon catheter.

In accompany with the guide wire 1 being thinned, the guiding catheter being also thinned from 7 F-8 F (2.3 mm-2.7 mm) to 5 F-6 F (1.59 mm-2.0 mm). This makes it possible to render the guide wire 1 minimally intrusive so as to lessen the burden which the patient suffers from when therapeutically treated.

Two sets of catheters in which the guide wire 1 is combined with the balloon catheter are prepared. Each set of the catheters is placed into the guiding catheter to implement the kissing manipulation in which balloons are concurrently inflated at a bifurcated portion of the vascular stenosis.

As apparent from the foregoing description, the core wire is wrought out near its limit so as to increase the tensile strength, and the melting heat of the eutectic alloy (welding member 4) is used to mutually solidify the core wire 2, the spring body 3 and head plug 5 at their welding section.

The film layer 44 is provided on the distal end portion 21 of the core wire 2 to improve the wetting property with the head plug 5, so as to solidify the head plug 5 which firmly welds the core wire 2 to the spring body 3 by means of the eutectic alloy. This further contributes to improve the mechanical strength of the guide wire 1 with the quality consistently stabilized despite the guide wire 1 is diametrically thinned.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:
1. A medical guide wire comprising:
a core wire formed of a flexible elongate member,
a helical spring body inserted to the core wire to be placed around the core wire, a welding member coated on an outer surface of a distal end portion of the core wire, a head plug provided on the welding member and fixing a distal end of the core wire and a distal end of the helical spring body, a front welding section fixed to the core wire and the helical spring body, the front welding section disposed on the core wire so that a distal end thereof is separated from a proximal end of the head plug, a proximal end of the welding member located between the proximal end of the head plug and the distal end of the front welding section, the core wire made of austenitic stainless steel wire treated with a solid solution procedure, and drawn with a whole cross sectional reduction ratio as 80%-97.6%; and the core wire and the helical spring body being partly welded by the welding member;

the welding member made of an eutectic alloy having a melting temperature ranging from 180° C.-495° C.

2. The medical guide wire according to claim 1, wherein the welding member and the head plug are formed of the identical or same type of eutectic alloy.

\* \* \* \* \*